United States Patent
Guo et al.

(10) Patent No.: US 10,243,160 B2
(45) Date of Patent: Mar. 26, 2019

(54) ORGANIC LIGHT EMITTING DEVICE, MANUFACTURING METHOD THEREOF AND DISPLAY APPARATUS

(71) Applicants: BOE TECHNOLOGY GROUP CO., LTD., Beijing (CN); HEFEI BOE OPTOELECTRONICS TECHNOLOGY CO., LTD., Hefei, Anhui (CN)

(72) Inventors: Yuanhui Guo, Beijing (CN); Hui Wang, Beijing (CN); Yuansheng Zang, Beijing (CN); Zhi Liu, Beijing (CN); Chun Wang, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 0 days.

(21) Appl. No.: 15/508,581

(22) PCT Filed: Jul. 25, 2016

(86) PCT No.: PCT/CN2016/091569
§ 371 (c)(1),
(2) Date: Mar. 3, 2017

(87) PCT Pub. No.: WO2017/080253
PCT Pub. Date: May 18, 2017

(65) Prior Publication Data
US 2017/0279069 A1 Sep. 28, 2017

(30) Foreign Application Priority Data
Nov. 11, 2015 (CN) .......................... 2015 1 0770974

(51) Int. Cl.
*H01L 51/52* (2006.01)
*H01L 51/56* (2006.01)
(Continued)

(52) U.S. Cl.
CPC ....... *H01L 51/5203* (2013.01); *A61M 1/0088* (2013.01); *H01L 29/43* (2013.01);
(Continued)

(58) Field of Classification Search
CPC ............. H01L 51/5228; H01L 51/5209; H01L 27/3281–27/329; H01L 51/5212–51/5215
See application file for complete search history.

(56) References Cited

U.S. PATENT DOCUMENTS

| 2005/0077814 | A1* | 4/2005 | Koo ................... H01L 27/3244 313/500 |
| 2009/0179208 | A1* | 7/2009 | Obata ................. H01L 51/0516 257/88 |
| 2009/0200921 | A1 | 8/2009 | Lee et al. |
| 2009/0224233 | A1 | 9/2009 | Obata et al. |

(Continued)

FOREIGN PATENT DOCUMENTS

| CN | 101013745 A | 8/2007 |
| CN | 101375428 A | 2/2009 |

(Continued)

OTHER PUBLICATIONS

The Second Chinese Office Action dated May 15, 2017; Appln. No. 201510770974.2.
(Continued)

*Primary Examiner* — Mariceli Santiago
(74) *Attorney, Agent, or Firm* — Ladas & Parry LLP

(57) ABSTRACT

An organic light emitting device and a manufacturing method thereof and a display apparatus are provided. The organic light emitting device includes a first electrode, a
(Continued)

second electrode, a third electrode and an organic material functional layer, and the organic material functional layer is disposed between the first electrode and the second electrode, the third electrode is disposed on a side of the first electrode close to the organic material functional layer; the third electrode is insulated from the first electrode, and part of the third electrode is overlapped with the first electrode; a distance between the first electrode and the second electrode is greater than a distance between the third electrode and the second electrode.

13 Claims, 3 Drawing Sheets

(51) Int. Cl.
*A61M 1/00* (2006.01)
*H01L 29/43* (2006.01)
*A61F 13/00* (2006.01)
*H01L 27/32* (2006.01)

(52) U.S. Cl.
CPC .... *H01L 51/5293* (2013.01); *A61F 13/00068* (2013.01); *H01L 27/32* (2013.01); *H01L 51/5262* (2013.01); *H01L 51/56* (2013.01)

(56) References Cited

U.S. PATENT DOCUMENTS

| | | | |
|---|---|---|---|
| 2011/0108877 A1* | 5/2011 | Yamada | H01L 27/3244 257/99 |
| 2012/0243219 A1 | 9/2012 | Ohsawa et al. | |
| 2014/0253856 A1* | 9/2014 | Nakahata | H01L 51/525 349/139 |
| 2014/0361256 A1 | 12/2014 | Kim et al. | |

FOREIGN PATENT DOCUMENTS

| | | |
|---|---|---|
| CN | 103296221 A | 9/2013 |
| CN | 203787435 U | 8/2014 |
| CN | 104037194 A | 9/2014 |
| CN | 104241537 A | 12/2014 |
| CN | 105280830 A | 1/2016 |
| CN | 205104520 U | 3/2016 |

OTHER PUBLICATIONS

First Chinese Office Action dated Oct. 9, 2016; Appln. No. 201510770974.2.
International Search Report and Written Opinion dated Oct. 28, 2016; PCT/CN2016/091569.

* cited by examiner

ORGANIC LIGHT EMITTING DEVICE, MANUFACTURING METHOD THEREOF AND DISPLAY APPARATUS

TECHNICAL FIELD

Embodiments of the present disclosure relate to an organic light emitting device, a manufacturing method thereof and a display apparatus.

BACKGROUND

Organic light emitting devices (OLEDs) can meet the requirements of low carbon environmental protection and green life for their various advantages such as solid-state luminous, wide viewing angle, low power consumption, fast response, high temperature resistance and low temperature resistance.

SUMMARY

Embodiments of the present disclosure provide an organic light emitting device, which includes a first electrode, a second electrode, a third electrode and an organic material functional layer, and the organic material functional layer is disposed between the first electrode and the second electrode, the third electrode is disposed on a side of the first electrode close to the organic material functional layer; the third electrode is insulated from the first electrode, and part of the third electrode is overlapped with the first electrode; a distance between the first electrode and the second electrode is greater than a distance between the third electrode and the second electrode.

In one embodiment of the present disclosure, for example, the organic material functional layer includes a hole transporting layer, a light emitting layer and an electron transporting layer.

In one embodiment of the present disclosure, for example, the electron transporting layer is arranged between the light emitting layer and the second electrode.

In one embodiment of the present disclosure, for example, the hole transporting layer is disposed between the third electrode and the light emitting layer.

In one embodiment of the present disclosure, for example, the organic material functional layer further includes a planarization layer disposed between the hole transporting layer and the third electrode.

In one embodiment of the present disclosure, for example, a thickness of the third electrode ranges from 5 nm to 20 nm.

In one embodiment of the present disclosure, for example, a material of the first electrode is the same as a material of the third electrode, and the material of the first electrode and the third electrode is selected from aluminum or copper.

In one embodiment of the present disclosure, for example, the planarization layer is made of a conductive polymer, and a thickness of the planarization layer ranges from 100 nm to 300 nm.

Embodiments of the present disclosure further provide a display apparatus, which includes any one of the above-mentioned organic light emitting device.

Embodiments of the present disclosure further provide a manufacturing method of an organic light emitting device, which includes: forming a first electrode on a base substrate through a patterning process; forming a third electrode on the base substrate through a patterning process, wherein the third electrode is insulated from the first electrode, and part of the third electrode is overlapped with the first electrode; forming an organic material functional layer and a second electrode sequentially on the base substrate formed with the third electrode; wherein a distance between the first electrode and the second electrode is greater than a distance between the third electrode and the second electrode.

BRIEF DESCRIPTION OF THE DRAWINGS

In order to clearly illustrate the technical solution of the embodiments of the disclosure, the drawings of the embodiments will be briefly described in the following, it is obvious that the described drawings are only related to some embodiments of the disclosure and thus are not limitative of the disclosure.

REFERENCE NUMERALS

01—first optical microcavity; 02—second optical microcavity; 10—base substrate; 11—first electrode; 12—second electrode; 13—third electrode; 14—insulating layer; 200—organic material functional layer; 20—light emitting layer; 201—first sub light emitting layer; 202—spacer layer; 203—second sub light emitting layer; 21—hole transporting layer; 22—electron transporting layer; 23—electron injection layer; 24—planarization layer; H1—distance between the first electrode and the second electrode; H2—distance between the third electrode and the second electrode.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Organic light emitting devices capable of emitting white light are widely used in the field of display or illumination. In order to adapt to the color temperature of the sunlight in different periods and different weather conditions, the color temperature of the white light emitted from the organic light emitting devices should be adjusted. For example, for the users living close to the equatorial, because the average color temperature of the sunlight (about 11000 K) is high, color temperature of the lighting device or display device should be increased; for the users living in the high latitude areas, because the average color temperature (about 5600 K) of the sunlight is low, displays or lighting devices with a low color temperature is more suitable.

In traditional approaches, regulating the light emitting color temperature can be achieved by regulating a voltage difference between the cathode and the anode of the organic light emitting devices. However, several defects exist in the traditional approaches: first, the color temperature range that can be regulated is too small; second, when a difference between two color temperatures is large, the voltage change is also great, thereby resulting in a large difference of the light emitting brightness of the organic light emitting devices.

Figure 1:
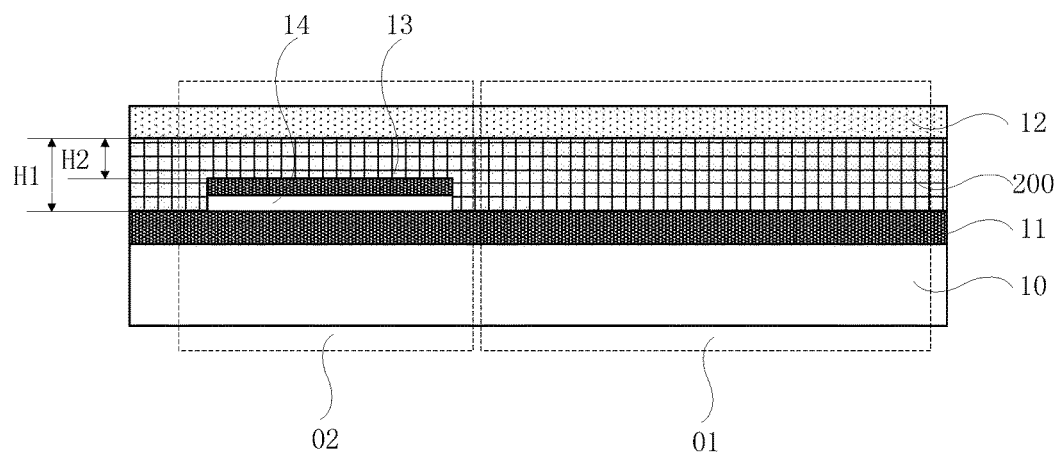
FIG. 1 is a schematic structure diagram of an organic light emitting device provided by an embodiment of the present disclosure.

Embodiments of the present disclosure provide an organic light emitting device, as shown in FIG. 1, the organic light emitting device comprises a first electrode 11, a second electrode 12 and an organic material functional layer 200 disposed between the first electrode 11 and the second electrode 12. For example, the organic light emitting device may further comprise a third electrode 13 disposed on a side of the first electrode 11, which side is close to the organic material functional layer 200.

The third electrode 13 is insulated from the first electrode 11. Part of the third electrode 13 is overlapped with the first electrode 11. For example, an insulating layer 14 can be disposed between the first electrode 11 and the third electrode 13. As shown in FIG. 1, a distance H1 between the first electrode 11 and the second electrode 12 is greater than a distance H2 between the third electrode 13 and the second electrode 12.

It should be noted that, first, the light emitting process of the organic light emitting device is: the positive carriers and the negative carriers encounter in the light emitting layer 20 of the organic material function layer 200 to form excitons, energy is transferred from the excitons to the organic light emitting material of the light emitting layer 20 through the recombination of the excitons, the atoms in the organic light emitting material are excited to transit from ground states to excited states, when the excited atoms return to the ground state, radiation transition takes place to emit light.

The carriers are generated by applying voltage between the first electrode 11 and the second electrode 12. For example, when the first electrode 11 is an anode, the first electrode 11 can generate positive carriers under the action of the external field voltage, those are holes. In this case, the second electrode 12 can be a cathode, the second electrode 12 can generate negative carriers under the action of the external field voltage, and those are electrons. For example, when the second electrode 12 is an anode, positive carriers can be generated under the action of the external field voltage, those are holes. In this case, the first electrode 11 can be a cathode, the first electrode 11 can generate negative carriers under the action of the external field voltage, and those are electrons. The first electrode 11 and the second electrode 12 are not limited in the present disclosure, and the following examples are illustrated by taking the first electrode 11 as the anode and the second electrode 12 as the cathode for example.

Second, the organic light emitting device can be a top-emitting or a bottom-emitting device. For example, for the top-emitting organic light emitting device, light is emitted through the second electrode 12. Therefore, the second electrode 12 may be made of a high transmittance and a high conductivity material. For example, the transparent conductive materials may be selected from at least one of indium tin oxide (short for ITO), or indium zinc oxide (short for IZO). The first electrode 11 may be made of a metal material having a high work function, for example, a material of the first electrode 11 can be selected from at least one of aluminum or silver.

In the case of the bottom-emitting organic light emitting device, light is emitted through the first electrode 11. Therefore, the first electrode 11 may be made of a high transmittance and a high conductivity material. For example, ITO or IZO and other transparent conductive materials. The second electrode 12 can be made of a metal material having a higher work function, for example, a material of the second electrode 12 can be selected from at least one of aluminum or silver.

The emitting-mode of the organic light emitting device is not limited in the embodiment of the present disclosure. The following examples are illustrated by the top-emitting organic light emitting devices.

Third, under the action of the external field voltage, the positive carriers emitted from the anode of the organic light emitting device and the negative carriers emitted from the cathode of the organic light emitting device are compounded in the light emitting layer 20 to generate energy, and the energy can be oscillated between the excited atoms and the photons radiated by the excited atoms at a certain frequency. In such a case, the photons are absorbed, reradiated and reabsorbed by the de-excitation atoms in the optical microcavity composed of the cathode and the anode, thus, the emission intensity at the emission peak can be enhanced by the optical microcavity.

The intensity $I_c(\lambda)$ of the spectrum emitted from the optical microcavity which is perpendicular to the light-emitting plane can be obtained by the following formula:

$$I_c(\lambda) = \frac{(1-R_d)\left[1+R_m+2[R_m]^{0.5}\cos\left[\frac{4\pi x}{\lambda}\right]\right]}{1+R_m R_d - 2(R_m R_d)^{0.5}\cos\left[\frac{4\pi L}{\lambda}\right]} \times |E_n(\lambda)|^2 \qquad (1)$$

In the above formula, $\lambda$ is the light emitting wavelength, x is the distance from the light emitting layer 20 to the metal electrodes (for example, the first electrode as the anode 11), $R_m$ and $R_d$ are the specular reflectances of the metal and the dielectric in the organic light emitting device respectively. $E_n(\lambda)$ is the distribution of the original spectrum (spectrum in free space).

It can be seen from the above formula, x determines the cavity length of the optical microcavity, and when x changes, the intensity $I_c(\lambda)$ of the spectrum emitted from the optical microcavity also changes, that is, the wavelength of the light emitted from the optical microcavity changes. In such a case, the color temperature of the light emitted from the organic light emitting device will also change.

Based on the above knowledge, as shown in FIG. 1, the organic light emitting device provided by the embodiment of the present disclosure comprises a first optical microcavity 01 composed of the first electrode 11 and the second electrode 12, and further comprises a second optical microcavity 02 composed of the third electrode 13 and the second electrode 12. Because the lengths of the first optical microcavity 01 and the second optical microcavity 02 are different, that is the distance H1 between the first electrode 11 and the second electrode 12 is greater than the distance H2 between the third electrode 13 and the second electrode 12, the color temperatures of the light emitted from the above two optical microcavities are different.

For example, since a distance from the first electrode 11 to the light emitting layer in the first optical microcavity 01 is greater than a distance from the third electrode 13 to the light emitting layer in the second optical microcavity 02, so the wavelength of the light emitted from the second optical microcavity 02 is shorter than the wavelength of the light emitted from the first optical microcavity 01. That is to say, the light emitted from the second optical microcavity 02 is blue-shifted, and the color temperature of the light is high; the light emitted from the first optical microcavity 01 is red-shifted, and the color temperature of the light is low. Besides, in the case that the area of the second electrode 12 and the voltage applied to the second electrode 12 remain unchanged, when the area of the first electrode 11 is increased, or the voltage applied to the first electrode 11 is increased, the color temperature of the light emitted from the first optical microcavity 01 is reduced, the emitted light is red-shifted. When the area of the third electrode 13 is increased, or the voltage applied to the third electrode 13 is increased, the color temperature of the light emitted from the second optical microcavity 02 is increased, the emitted light is blue-shifted. The color temperature of the mixed light emitted from the two optical microcavities is the color temperature of the light emitted from the organic light emitting device.

Therefore, before the products are delivered, according to the users' requirements, the color temperature of light emitted from the organic light emitting device can be customized by controlling the area of the first electrode 11 or the third electrode 13 in the preparation process of the organic light emitting devices.

After the products are delivered, though the area of the first electrode 11 or the third electrode 13 has been fixed, the color temperature of the emitting light from the first optical microcavity 01 or the second optical microcavity 02 can also be changed by adjusting the voltage applied to the first electrode 11, the third electrode 13 or the second electrode 12, and ultimately the color temperature of the light emitted from the organic light emitting device is changed. For example, in the case that the voltage applied to the second electrode 12 remains unchanged, the voltage V1 applied to the first electrode 11 is 10 V, the voltage V2 applied to the third electrode 13 is 0 V, the color temperature of the emitting light of the organic light emitting device is 3000 K; when V1 decreases to 8 V, and V2 increases to 10 V, the color temperature of the emitting light of the organic light emitting device is 5000 K; when V1 decreases to 0 V, and V2 remains 10V, the light emitting color temperature of the organic light emitting device is 7000 K. The above are the examples of adjusting the color temperature of the organic light emitting device, and other detailed examples will be omitted.

It is clear from the above descriptions, when the second electrode 12 acts as the cathode of the first optical microcavity 01 and the second optical microcavity 02, the first electrode 11 acts as the anode of the first optical microcavity 01, and the third electrode 13 acts as the anode of the second optical microcavity 02. In this case, for example, a material of the third electrode 13 and a material of the first electrode 11 may be the same material. For example, a material of the third electrode 13 may be any one selected from aluminum or copper.

Further, a thickness of the third electrode 13 may ranges from 5 nm to 20 nm. When the thickness of the third electrode 13 is less than 5 nm, the conductivity of the third electrode 13 will decrease, the third electrode 13 is unable to provide enough carriers (such as holes) to the light emitting layer 20 under the action of the external electric field; when the thickness of the third electrode 13 is greater than 20 nm, the whole thickness of the organic light emitting device is increased because the thickness of the third electrode 13 is large, which is harmful to the ultra-thin design of the organic light emitting device.

Embodiments of the present disclosure provide an organic light emitting device, which comprises a first electrode, a second electrode and a organic material functional layer disposed between the first electrode and the second electrode. The organic light emitting device may further comprise a third electrode disposed on a side of the first electrode close to the organic material functional layer. The third electrode is insulated from the first electrode and part of the third electrode is overlapped with the first electrode. A distance between the first electrode and the second electrode is greater than a distance between the third electrode and the second electrode.

As a result, a first optical microcavity is formed between the first electrode and the second electrode, and a second optical microcavity is formed between the third electrode and the second electrode. Because the distance from the first electrode to the second electrode is greater than the distance from the third electrode to the second electrode, in this case, when a voltage is applied to the first electrode, the second electrode and the third electrode respectively, the first optical microcavity and the second optical microcavity can emit light of different wavelengths.

Based on the above, after light emitted from the first optical microcavity with a first color temperature and light emitted from the second optical microcavity with a second color temperature are superimposed, light having a third color temperature emits out from the organic light emitting device. The first color temperature, the second color temperature and the third color temperature are different from each other. So that, both the first color temperature and the second color temperature can affect the third color temperature, thus the adjusting range of the color temperature of the organic light emitting device is increased.

In addition, because the third color temperature is formed by superimposing the first color temperature and the second color temperature, a substantial adjustment of the third color temperature can be achieved only by a little change of the first color temperature and the second color temperature. When the first color temperature and the second color temperature are slightly changed, the electrode voltage values of the first optical microcavity and the second optical microcavity do not need to be changed greatly, so that before and after adjusting the color temperature, the brightness of the organic light emitting devices will not show a big difference.

Figure 2:
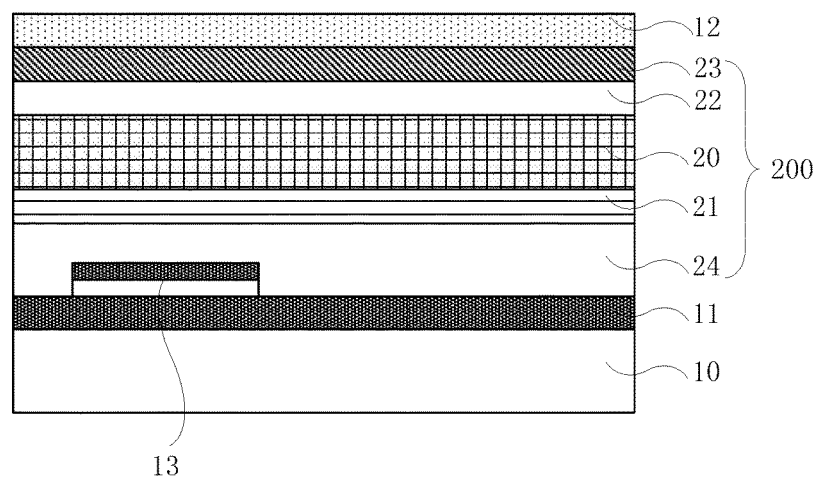
FIG. 2 is a schematic structure diagram of the organic light emitting device illustrated in FIG. 1 with additional functional layers.

As shown in FIG. 2, in addition to the light emitting layer 20, the organic material functional layer 200 further comprises a hole transporting layer 21 and an electron transporting layer 22. The structure of the organic functional layer 200 will be illustrated in the following by giving examples.

As shown in FIG. 2, in order to improve the carriers (such as holes) transporting capacity of the first electrode 11 and the third electrode 13 under an external electric field, a hole transport layer 21 may be disposed between the third electrode 13 and the light emitting layer 20.

Or, in order to improve the carriers (such as electrons) transporting capacity of the second electrode 12 under an external electric field, an electron transport layer 22 may be disposed between the second electrode 12 and the light emitting layer 20.

In addition, in order to improve the ability of injecting carriers (such as electrons) from the second electrode 12 into the light emitting layer 20, the organic functional layer 200 for example can further comprise an electron injection layer 23, and the electron injection layer 23 is disposed between the second electrode 12 and electron transporting layer 22.

In such a case, as shown in FIG. 2, since the third electrode 13 protrudes from the first electrode 11, in order to make the surface of the rest layers disposed above the third electrode 13 flat, the organic material functional layer 200 may also comprise a planarization layer 24, and the planarization layer 24 is disposed between the hole transport layer 21 and the third electrode 13.

For example, the planarization layer 24 may be made of a conductive polymeric material, for example PEDOT:PSS, the PEDOT is a polymer of the EDOT (3, 4-ethylene oxide monomer), and the PSS is polystyrene sulfonate. In this case, the planarization layer 24 may play the roles of conduction and holes injection.

For example, a thickness of the planarization layer 24 ranges from 100 nm to 300 nm. When the thickness of the planarization layer 24 is less than 100 nm, because the planarization layer 24 is too thin, the flattening effect is not good enough. When the thickness of the planarization layer 24 is greater than 300 nm, the thickness of the device will be increased, which is harmful to the ultra-thin design of the organic light emitting device.

Embodiments of the present disclosure provide a display apparatus, which comprises any one of the above-described organic light emitting device. The organic light emitting device included in the display apparatus has the same structure and beneficial effects with the organic light emitting device provided in the above embodiments, because the structure and beneficial effects of the organic light emitting device have been illustrated in detail in the aforementioned embodiments, and detailed descriptions will be omitted.

It should be noted that, in the embodiment of the present disclosure, the display apparatus can be an organic light emitting diode display apparatus, for example, the display apparatus can be a television, a digital picture frame, a mobile phone or a tablet computer and any other product or component having a display function.

Figure 3:
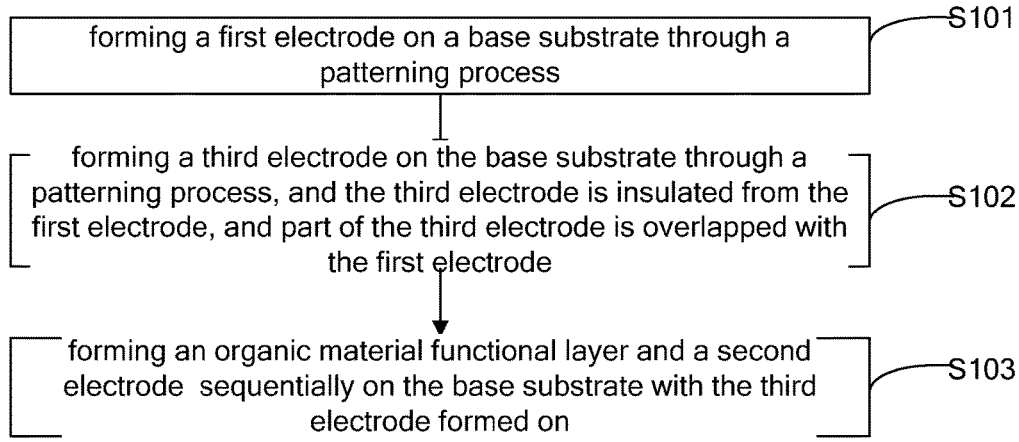
FIG. 3 is a flow chart of a manufacturing method of an organic light emitting device provided by an embodiment of the present disclosure.

Embodiments of the present disclosure provide a manufacturing method of an organic light emitting device, as shown in FIG. 3, the method includes:

S101, forming a first electrode 11 on a base substrate 10 illustrated in FIG. 1 through a patterning process;

S102, forming a third electrode 13 on the base substrate 10 through a patterning process, and part of the third electrode 13 is overlapped with the first electrode 11, and the third electrode 13 is insulated from the first electrode 11.

For example, an insulating layer 14 can be formed on the base substrate 10 with the first electrode 11 formed on through a patterning process, then the third electrode 13 is formed on the base substrate 10 with the insulating layer 14 formed on through a patterning process. The insulating layer 14 can cover the first electrode 11 completely, and the insulating layer 14 can also be formed only at the overlapped areas between the third electrode 13 and the first electrode 11.

S103, forming an organic material functional layer and a second electrode 12 sequentially on the base substrate with the third electrode 13 formed on.

Wherein, a distance between the first electrode 11 and the second electrode 12 H1 is greater than a distance between the third electrode 13 and the second electrode 12 H2.

It should be noted that, in the patterning process of the embodiment of the present disclosure, the patterning process can only include a photolithography process, or include a photolithography and etching processes, or at the same time, can also include printing, inkjet and other processes for forming a predetermined pattern. The photolithography process is the process of forming a pattern by using a photoresist, a mask, an exposure machine and so on, and the photolithography process includes the processes of forming film, exposure, development and so on. The corresponding patterning process can be selected according to the structure formed in the embodiment of the present disclosure.

In addition, the one patterning process in the present disclosure, for example, refers to forming different exposure areas through a mask exposure process, and then the different exposure regions are treated by multiple etching, ashing and other removal processes, and finally the expected patterns are obtained.

As a result, a first optical microcavity is formed between the first electrode and the second electrode, and a second optical microcavity is formed between the third electrode and the second electrode. Because the distance from the first electrode to the second electrode is greater than the distance from the third electrode to the second electrode, in such a case, when a voltage is applied to the first electrode, the second electrode and the third electrode respectively, the first optical microcavity and the second optical microcavity can produce light with different wavelengths.

Based on the above, after light emitted from the first optical microcavity with a first color temperature and light emitted from the second optical microcavity with a second color temperature are superimposed, light having a third color temperature emits out from the organic light emitting device. The first color temperature, the second color temperature and the third color temperature are different from each other. So that, both the first color temperature and the second color temperature can affect the third color temperature, thus the adjusting range of the color temperature of the organic light emitting device is increased.

In addition, because the third color temperature is formed by superimposing the first color temperature and the second color temperature, a substantial adjustment of the third color temperature can be achieved only by a little change of the first color temperature and the second color temperature. When the first color temperature and the second color temperature are slightly changed, the electrode voltage values of the first optical microcavity and the second optical microcavity do not need to be changed greatly, so that before and after adjusting the color temperature, the brightness of the organic light emitting devices will not show a big difference.

Figure 4:
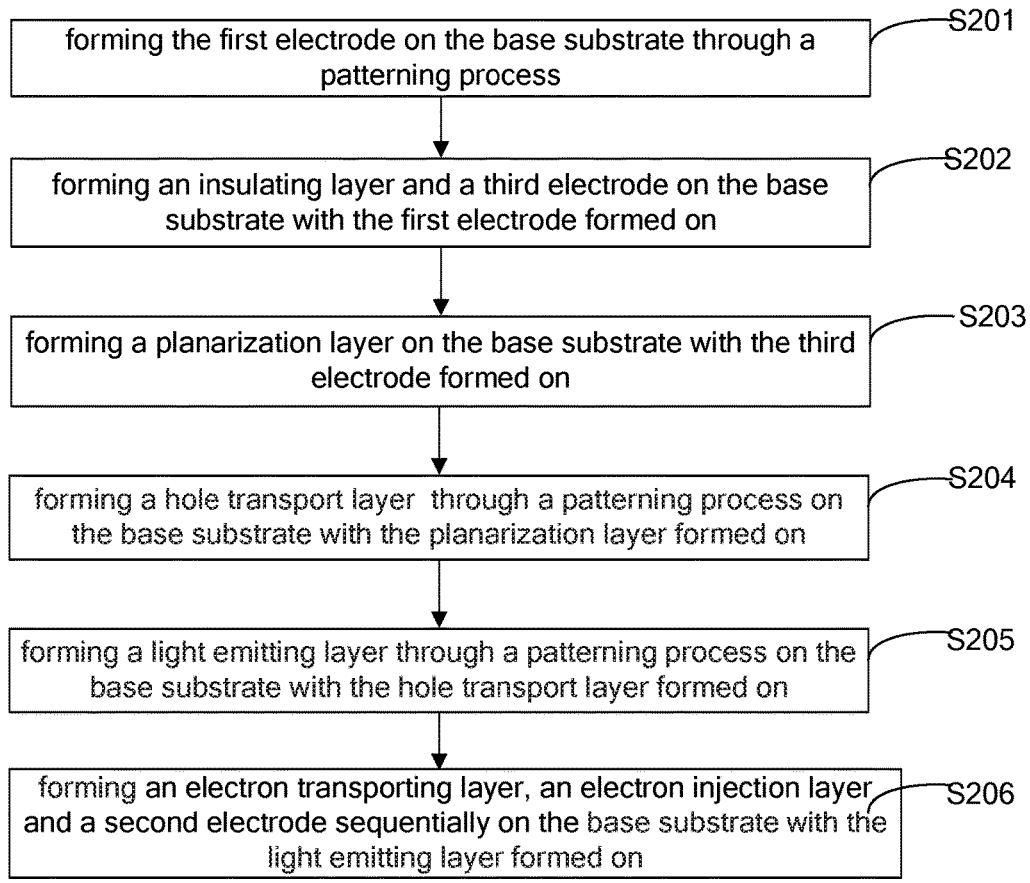
FIG. 4 is a flow chart of a manufacturing method of the organic light emitting device illustrated in FIG. 2.

The fabrication process of the organic light emitting devices shown in FIG. 2 will be illustrated in following, for example, as shown in FIG. 4.

S201, forming a first electrode 11 on a base substrate 10 through a patterning process;

For example, a metal thin film layer with a thickness ranges from 10 nm to 300 nm is coated on a surface of a glass substrate or a resin substrate, for example 150 nm. The metal thin film layer is made of a metal material with high work function, such as any one of aluminum or silver.

S202, forming an insulating layer 14 and a third electrode 13 on the base substrate 10 with the first electrode 11 formed on.

For example, firstly, a high insulating thin film layer is coated on a surface of the first electrode 11, for example, a silicon oxide thin film layer. A thickness of the silicon oxide thin film layer ranges from 5 nm to 20 nm, for example 20 nm. Then an aluminum thin film layer or a silver thin film layer is coated on a surface of the silicon oxide thin film layer whose thickness ranges from 5 nm to 20 nm, for example 10 nm. Then through a patterning process, the insulating layer 14 and the third electrode 13 with a same pattern are formed.

S203, forming a planarization layer 24 on the base substrate with the third electrode 13 formed on.

For example, coating a conductive polymer on the base substrate with the third electrode 13 formed on, for example PEDOT:PSS with a thickness ranges from 100 nm to 300 nm, for example 200 nm, to form a smooth planarization layer 24. The good conductivity of the planarization layer 24 is favorable to the injection of holes.

S204, forming a hole transport layer 21 through a patterning process on the base substrate with the planarization layer 24 formed on.

For example, the hole transport layer 21 is made of N,N'-di(1-naphthyl)-N,N'-diphenyl-1,1'-biphenyl-4-4'-diamine composition with a thickness ranges from 5 nm to 50 nm, for example 10 nm.

S205, forming a light emitting layer through a patterning process on the base substrate with the hole transport layer 21 formed on.

Figure 5:
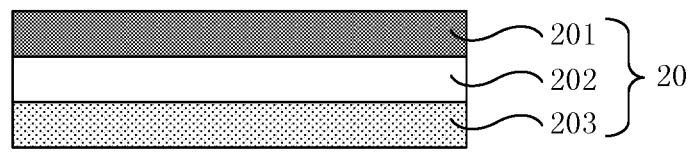
FIG. 5 is a schematic structure diagram of the light emitting layer illustrated in FIG. 1 or FIG. 2.

For example, the light emitting layer 20 can be composed of a single layer thin film layer and can also be composed of multiple film layers as shown in FIG. 5, with a thickness ranges from 5 nm to 50 nm.

For example, for the light emitting layer 20 composed of multiple film layers, the light emitting layer 20 includes a first sub light emitting layer 201, a spacer layer 202 and a second sub light emitting layer 203.

The first sub light emitting layer 201 for example, is a red or an orange light emitting layer with a thickness of 5 nm; the host material is 4,4'-di(9-carbazole) biphenyl, 4,4'-dicarbazole-9-biphenyl, the guest material is acetylacetone di(2-methyl) dihenzo [F, H] quinoxaline iridium, and the doping amount of the guest material is 0.5 wt %. The spacer layer 202 for example has a thickness of 5 nm. The second sub light emitting layer 203 for example is a blue sub light emitting layer has a thickness of 25 nm, the host material is 4,4'-di(9-carbazole) biphenyl, 4,4'-dicarbazole-9-biphenyl, the guest material is bis(4,6-difluoro pyridine-N, C2)-Pyridinium Iridium, and the doping amount of the guest material is 10 wt %.

The light emitting layer 20 further comprises a red sub light emitting layer, a blue sub light emitting layer and a green sub light emitting layer and so on.

S206, forming an electron transporting layer 22, an electron injection layer 23 and a second electrode 12 sequentially on the base substrate with the light emitting layer 20 formed on.

For example, a material of the electron transporting layer 22 may be Bphen (4,7-diphenyl-1,10-phenanthrine) with a thickness ranges from 5 nm to 50 nm, for example 40 nm.

A material of the second electrode layer 12 may be a transparent conductive material, such as ITO or IZO, with a thickness ranges from 10 nm to 20 nm, for example 10 nm.

What are described above is related to the illustrative embodiments of the disclosure only and not limitative to the scope of the disclosure; the scopes of the disclosure are defined by the accompanying claims.

The present application claims the priority of the Chinese Patent Application No. 201510770974.2 filed on Nov. 11, 2015, which is incorporated herein by reference as part of the disclosure of the present application.

What is claimed is:

1. An organic light emitting device, comprising: a first electrode, a second electrode, a third electrode and an organic material functional layer, wherein the organic material functional layer is disposed between the first electrode and the second electrode, the third electrode is disposed on a side of the first electrode close to the organic material functional layer;
   the third electrode is insulated from the first electrode, and part of the third electrode is overlapped with the first electrode;
   a distance between the first electrode and the second electrode is greater than a distance between the third electrode and the second electrode;
   wherein the organic material functional layer comprises a hole transporting layer, a light emitting layer and an electron transporting layer, the light emitting layer is disposed between the third electrode and the second electrode;
   the organic material functional layer further comprises a planarization layer disposed between the hole transporting layer and the third electrode, and the material of the planarization layer comprises PEDOT:PSS.

2. The organic light emitting device according to claim 1, wherein the electron transporting layer is disposed between the light emitting layer and the second electrode.

3. The organic light emitting device according to claim 1, wherein the hole transporting layer is disposed between the third electrode and the light emitting layer.

4. The organic light emitting device according to claim 1, wherein a thickness of the third electrode ranges from 5 nm to 20 nm.

5. The organic light emitting device according to claim 1, wherein a material of the first electrode is the same as a material of the third electrode, and the material of the first electrode and the third electrode is selected from aluminum or copper.

6. The organic light emitting device according to claim 1, wherein a material of the planarization layer comprises a conductive polymer, and a thickness of the planarization layer ranges from 100 nm to 300 nm.

7. A display apparatus, comprising the organic light emitting device according to claim 1.

8. A display apparatus, comprising the organic light emitting device according to claim 2.

9. A display apparatus, comprising the organic light emitting device according to claim 3.

10. A display apparatus, comprising the organic light emitting device according to claim 4.

11. A display apparatus, comprising the organic light emitting device according to claim 5.

12. A display apparatus, comprising the organic light emitting device according to claim 6.

13. A manufacturing method of an organic light emitting device, comprising:
   forming a first electrode on a base substrate through a first patterning process;
   forming a third electrode on the base substrate through a second patterning process, wherein the third electrode is insulated from the first electrode, and part of the third electrode is overlapped with the first electrode; and
   forming an organic material functional layer and a second electrode sequentially on the base substrate formed with the third electrode; wherein a distance between the first electrode and the second electrode is greater than a distance between the third electrode and the second electrode;
   wherein the organic material functional layer comprises a hole transporting layer, a light emitting layer and an electron transporting layer, the light emitting layer is disposed between the third electrode and the second electrode;

the organic material functional layer further comprises a planarization layer disposed between the hole transporting layer and the third electrode, and the material of the planarization layer comprises PEDOT:PSS.

* * * * *